(12) United States Patent
Chen et al.

(10) Patent No.: US 12,291,449 B2
(45) Date of Patent: May 6, 2025

(54) BLACK PHOSPHORUS NANOSHEET, PREPARATION METHOD THEREFOR, AND APPLICATION THEREOF

(71) Applicant: SINOSTEEL NANJING ADVANCED MATERIALS RESEARCH INSTITUTE CO., Ltd., Nanjing (CN)

(72) Inventors: Jie Chen, Nanjing (CN); Yanhua Luo, Nanjing (CN); Xiaodong Pei, Nanjing (CN); Fan Wang, Nanjing (CN); Fenglin Tang, Nanjing (CN); Yefeng Zhu, Nanjing (CN); Baojin Shen, Nanjing (CN); Xiuguang Yang, Nanjing (CN); Ling Zhang, Nanjing (CN)

(73) Assignee: SINOSTEEL NANJING ADVANCED MATERIALS RESEARCH INSTITUTE CO., LTD., Nanjing (CN)

( * ) Notice: Subject to any disclaimer, the term of this patent is extended or adjusted under 35 U.S.C. 154(b) by 313 days.

(21) Appl. No.: 17/763,153

(22) PCT Filed: Jun. 2, 2020

(86) PCT No.: PCT/CN2020/093829
§ 371 (c)(1),
(2) Date: Mar. 23, 2022

(87) PCT Pub. No.: WO2021/237763
PCT Pub. Date: Dec. 2, 2021

(65) Prior Publication Data
US 2023/0075308 A1    Mar. 9, 2023

(30) Foreign Application Priority Data
May 27, 2020   (CN) .......................... 202010461825.9

(51) Int. Cl.
*C01B 25/02* (2006.01)
*B82Y 30/00* (2011.01)
*B82Y 40/00* (2011.01)

(52) U.S. Cl.
CPC ............... *C01B 25/02* (2013.01); *B82Y 30/00* (2013.01); *B82Y 40/00* (2013.01)

(58) Field of Classification Search
None
See application file for complete search history.

(56) References Cited

U.S. PATENT DOCUMENTS 10,121,658 B2    11/2018  Kwon et al.
10,343,909 B2 *   7/2019  Hersam .................. B82Y 10/00

FOREIGN PATENT DOCUMENTS

| CN | 104876199 | A  |    | 9/2015  |
|----|-----------|----|----|---------|
| CN | 104903379 |    | *  | 9/2015  |
| CN | 105236366 | A  |    | 1/2016  |
| CN | 104779380 | B  |    | 3/2017  |
| CN | 107275119 | A  |    | 10/2017 |
| CN | 109019540 | A  |    | 12/2018 |
| CN | 108192145 |    | *  | 11/2019 |
| CN | 110527251 |    | *  | 12/2019 |
| CN | 110627028 | A  |    | 12/2019 |
| CN | 110817816 | A  |    | 2/2020  |
| IN | 109368607 | A  |    | 2/2019  |
| KR | 20170102771 | A |   | 9/2017  |
| WO | 2019144609 |   | *  | 8/2019  |
| WO | 201937188 | A1 |    | 12/2019 |

OTHER PUBLICATIONS

Ambrosi et al. "Electrochemical Exfoliation of Layered Black Phosphorus into Phosphorene," Angewandte Chemie Int Ed, Jul. 21, 2017, pp. 10443-10445, vol. 56(35).

Yang et al. "A Delamination Strategy for Thinly Layered Defect-Free High-Mobility Black Phosphorus Flakes," Angewandte Chemie Int Ed, Feb. 23, 2018, pp. 4677-4681, vol. 57.

* cited by examiner

*Primary Examiner* — Sheng H Davis (57) ABSTRACT

The present invention relates to a method of preparing a black phosphorus nanosheet and application, belonging to the technical field of functional material production. In the method, the black phosphorus sheet is used as the electrolytic anode, and an electrochemical reaction system is constructed together with an inert electrode and an alkaline aqueous electrolyte, wherein the alkaline aqueous electrolyte comprises an N-N dimethylformamide solution dissolved with epoxy resin. In alkaline aqueous electrolyte, the prepared black phosphorus nanosheet structure tends to be more stable, not easy to be damaged and the oxidation degree is reduced. Under alkaline conditions, it is conducive to improve the intercalation and stripping effect of black phosphorus material of anode and make the black phosphorus exfoliation more complete.

15 Claims, 7 Drawing Sheets

BLACK PHOSPHORUS NANOSHEET, PREPARATION METHOD THEREFOR, AND APPLICATION THEREOF

TECHNICAL FIELD

The invention belongs to the technical field of functional material production, more specifically relates to a black phosphorus nanosheet and a preparation method thereof. The black phosphorus nanosheet is suitable for two-dimensional semiconductor materials and biomedical carriers of high-performance electronic and optoelectronic devices.

RELATED ART

In recent years, black phosphorene (also known as black phosphorus nanosheets) with single-layer or few layers of black phosphorus atomic layer structure has gradually become the most potential two-dimensional semiconductor materials for high-performance electronic and optoelectronic devices because of their high carrier mobility ($200~1000$ $cm^2v^{-1}s^{-1}$), adjustable direct bandgap, large switching ratio ($10^4~10^5$) and anisotropy. The atomic layers of black phosphorus are also stacked with each other through weak interlayer force, and this force has the characteristics of van der Waals force. Therefore, mechanical exfoliation (tape tearing method) has become a reliable laboratory technology to prepare a very small amount of high-quality black phosphorus nanosheets. A large number of two-dimensional materials can be prepared by the chemical exfoliation method, but this method will introduce defects or phase transition, resulting in the decline of the electrical properties of two-dimensional materials, so it is not suitable for the preparation of high-quality black phosphorus nanosheets. Recently, liquid phase ultrasonic exfoliation is considered to be an effective way to prepare high-quality black phosphorus nanoparticles, and this method will not produce intermediate chemical reactions, but its disadvantage is that the exfoliation effect will be limited by the energy of the ultrasonic used and the lengthy exfoliation time. It is still a challenge to develop a preparation strategy with a high intrinsic degree, high yield, and environment-friendly. The low-cost large-scale preparation of black phosphorus nanosheets through principle innovation and process technology improvement is still an important research topic in the field of black phosphorus nanosheet materials.

Many works have reported the method of preparing black phosphorus nano tablets. For example, Publication No. US20180138039A1 uses ultraviolet radiation to peel off black phosphorus and obtains black phosphorus nano tablets with fewer layers and low oxidation degree. However, due to the complex process and the need for high-intensity ultraviolet rays that are harmful to the human body, it is difficult to scale up in industrialization. Publication No. CN105236366A uses the liquid-phase shear force generated by the high-speed rotating cutter head to peel the black phosphorus crystal to obtain the dispersion of the black phosphorus nanosheet. Finally, a clean black phosphorus nanosheet can be obtained by centrifugation, filtration, and cleaning. However, due to the poor process, the exfoliation effect is limited. Publication No. CN104876199A discloses a method for preparing a few-layer black phosphorus sheet by ultrasonic exfoliation of black phosphorus. The black phosphorus powder is intercalated with an intercalating agent. After isolation from the air, the few-layer black phosphorus sheet material is obtained by ultrasonic water bath exfoliation and vacuum drying. The ultrasonic exfoliation method is carried out under the condition of isolation from the air. During the reaction process, It is necessary to control the oxygen and water content in the solution, which has high requirements and high energy consumption and can not meet the requirements of industrial production. The electrochemical exfoliation method is also a common method, but most electrochemical exfoliation methods use organic electrolytes because black phosphorus is prone to oxidation in an aqueous solution. Publication No. CN109019540A discloses a method for preparing black phosphorus nano tablets by electrolytic exfoliation in high concentration (0.1~15 m) onium cationic salt solution. However, many organic solvents with high viscosity are involved in the process, which brings difficulties to the subsequent treatment. Publication No. CN104779380A discloses a method for preparing phosphorene by electrochemistry. The electrolytic cell is assembled with the inert electrode as a positive electrode and phosphorus as a negative electrode. DC or AC voltage is applied between the two stages of the electrolytic cell to peel it into phosphorene under the action of the electric field. However, cations are mainly intercalated at the cathode, while most cations in the aqueous electrolyte are Li+/Na+, the intercalation effect is very limited, and the exfoliation process is more difficult to control. Publication No. CN110627028A discloses a preparation method of two-dimensional ultra-thin black phosphorus using organic solvent rich in hydroxyl functional groups as a source and introducing hydroxyl groups. The hydroxyl functional groups are introduced on the surface of black phosphorus by organic solvent to make it stable in air.

In addition, Ambrosi (Angew Chem Int Edit, 2017, 5610443) and others use electrolytic methods to prepare black phosphorus crystals in sulfuric acid solution. The oxidation degree of black phosphorus obtained is very high, which does not meet the application requirements of high-end products. Yang (Angew Chem Int Edit, 2018, 574677) and others have reduced the oxidation degree of black phosphorus nanosheets by cathodic electrochemical exfoliation of black phosphorus crystals, but their size and thickness can not be controlled, and the process is difficult to scale up due to the need for the expensive organic salt solution.

To sum up, due to the high cost of organic electrolytes at present, there will be many difficulties in industrial amplification operation, and the aqueous electrolyte is prepared with the acidic solution or neutral electrolyte, resulting in a high oxidation degree of black phosphorus, which is difficult to meet the application of subsequent high-end products.

SUMMARY

Aiming at the problem of high oxidation degree of black phosphorus caused by preparing black phosphorus nanosheet in aqueous electrolyte, the invention provides a preparation method of black phosphorus nanosheet and the obtained black phosphorus nanosheet. The black phosphorus nanosheet has low oxygen content, few layers, and superior service performance.

The invention also provides an application of the black phosphorus nanosheet on a two-dimensional semiconductor material.

To solve the above problems, the technical scheme adopted by the invention is as follows:

The preparation method of the black phosphorus nanosheet of the invention takes the black phosphorus sheet as the electrolytic anode and constructs an electrochemical reaction system together with an inert electrode and an alkaline aqueous electrolyte, wherein the alkaline aqueous electrolyte comprises an N-N dimethylfonnamide solution dissolved with epoxy resin.

Further, the preparation method of the black phosphorus nanosheet comprises the following specific steps:

Step S101: electrode selection

Black phosphorus sheet is used as electrolytic anode; Inert electrode is selected as electrolytic cathode;

Step S102: prepare alkaline aqueous electrolyte

1) Prepare 0.1~2 mol/L sulfate solution A and 0.1~2 mol/L sulfate solution B, add alkaline solution to the sulfate solution B, adjust the pH value of sulfate solution B to 8~14, and mix evenly to obtain alkaline aqueous electrolyte C;

2) Prepare N-N dimethylformamide solution with epoxy resin dissolved;

Step S103: reaction and exfoliation

In a constant temperature environment of 0~10° C., with black phosphorus sheet as an anode, inert electrode as a cathode, and sulfate solution A as the electrolyte, the surface current density is controlled at 200~500 mA/din' under a DC voltage of 2.5~3.5V and maintained stably for 1~3 h; Then, the anode and cathode are transferred to alkaline aqueous electrolyte C. At the same time, N-N dimethylformamide solution dissolved with epoxy resin is added to alkaline aqueous electrolyte C, the voltage is stable at 5~10V, the distance between electrodes remains unchanged, the area current density is controlled at 600~900 mA/dm$^2$, then powered on for 0.5~1.5 h, and the black phosphorus nanosheet precipitation is obtained at the bottom of alkaline aqueous electrolyte C.

In a possible embodiment of the invention, the epoxy resin is E44 or E51, wherein the mass ratio of epoxy resin to N-N dimethylformamide is 0.1~2%, preferably 0.5~1%.

In a possible embodiment of the invention, the volume ratio of the N-N dimethylformamide solution dissolved with epoxy resin to the alkaline aqueous electrolyte C is 1:50~1:200, and the preferred volume ratio is 1:100~1:120.

In a possible embodiment of the invention, the black phosphorus sheet is pressed by the black phosphorus material through the tablet pressing equipment, and the black phosphorus material is one or more of the black phosphorus single crystal and black phosphorus powder.

In a possible embodiment of the invention, the sulfate is selected from one or more ammonium sulfate, ammonium bisulfate, sodium sulfate, sodium bisulfate, potassium sulfate, and potassium bisulfate.

In a possible embodiment of the invention, the alkaline solution is ammonia, sodium hydroxide solution, or potassium hydroxide solution, preferably the alkaline solution is ammonia, add ammonia to sulfate solution B, adjust the pH value to 8~10, and stir the mixture at an average speed for 15~20 minutes; Ultrasonication was performed at 15~30° C. and 30~60 W for 1~10 minutes.

In a possible embodiment of the invention, the inert electrode is a platinum electrode, a gold electrode, or a carbon rod.

Further, the preparation method of the black phosphorus nanosheet also includes the following steps:

Step S104: cleaning and extraction Dissolve the precipitate obtained in step S103 in an organic solvent, and ultrasonic for 20 to 40 minutes at a power of 30 to 100 W at room temperature to obtain solution D; Centrifuge the D solution At a rate of 2000~4000 rpm for 20~40 minutes; The upper liquid after centrifugation is filtered and cleaned with deionized water for 5~10 times to obtain the separated solid.

In a possible embodiment of the invention, the organic solvent in step S104 is one or more of N-N dimethylformamide, N-methylpyrrolidone, dimethyl sulfoxide, and isopropanol; The amount of the organic solvent is 1~2 ml/mg of the precipitate obtained by the exfoliation reaction in step S103.

In a possible embodiment of the invention, the lower precipitate after centrifugation can be cleaned and recovered and can be reused for the anode in preparation step S101.

Further, the electrochemical preparation method of the black phosphorus nanosheet also includes the following steps:

Step S105: drying

The solid separated in step S104 is dried to obtain black phosphorus nanosheets.

In a possible embodiment of the invention, the drying method in step S105 is vacuum drying or freeze drying.

The invention also relates to a black phosphorus nanosheet prepared by any of the above methods. The obtained black phosphorus nanosheet is not an oxidized black phosphorus nanosheet, but an intrinsic black phosphorus nanosheet with a low oxygen degree. Its oxygen content is low, and the proportion of oxygen element to the total mass of black phosphorus nanosheet does not exceed 15%; The size of the prepared black phosphorus nanosheet is large, not less than 1 μm; The layer-number of phosphorene is less than 10.

Beneficial effects: Compared with the prior art, the beneficial effects of the invention are:

(1) The preparation method of the invention takes the black phosphorus sheet as the electrolytic anode, and the alkaline aqueous electrolyte contains N-N dimethylformamide solution dissolved with epoxy resin, the structure of the prepared black phosphorus nanosheet tends to be more stable in the alkaline aqueous electrolyte, not easy to be damaged and the oxidation degree is reduced. Under alkaline conditions, it is beneficial to improve the intercalation exfoliation effect of the black phosphorus material of the anode, which makes the black phosphorus exfoliation more complete;

(2) In the preparation method of the invention, the pH regulating solution adopted by the alkaline aqueous electrolyte is ammonia, which can provide an alkaline atmosphere on the one hand, and on the other hand, the subsequent thorough removal is more convenient. If alkaline reagents such as sodium hydroxide and potassium hydroxide are used, there will be some residues in the subsequent cleaning, which will affect the purity of the obtained black phosphorus nano tablets; In the process of thermal evaporation, ammonia will be discharged from the black phosphorus layers, which will help the black phosphorus exfoliation and further reduce the number of layers of the exfoliated black phosphorus nanosheets;

(3) Compared with the current situation of mass production of black phosphorus nanosheet with high oxidation degree, small size, and many layers, the maximum oxygen content of the black phosphorus nanosheet obtained by the preparation method of the invention does not exceed 20%, the average size exceeds 2 μm, and the number of layers is less than 10, which is conducive to improve and realize the low-cost large-scale preparation of high intrinsic black phosphorus nanoparticles.

DESCRIPTION OF EMBODIMENTS

The preparation method of the black phosphorus nanosheet of the invention takes the black phosphorus sheet as the electrolytic anode and constructs an electrochemical reaction system together with an inert electrode and an alkaline aqueous electrolyte. The inert electrode can be a platinum electrode, a gold electrode, or a carbon rod, wherein the alkaline aqueous electrolyte contains N-N dimethylformamide solution dissolved with epoxy resin.

Wherein the epoxy resin is E44 or E51, wherein the mass ratio of epoxy resin to N-N dimethylformamide is 0.1~2%, preferably 0.5~1%. The volume ratio of the N-N dimethylformamide solution dissolved with epoxy resin to the alkaline aqueous electrolyte C is 1:50~1:200, and the preferred volume ratio is 1:100~1:120. The inventor has proved through a large number of tests that the better addition amount of epoxy resin is 0.1~2%, which has little effect in this range, but more than 2% will affect the conductivity of the electrolyte.

It should be noted that the time of black phosphorus electrolysis reaction is short, and there is a problem that oxidation and decomposition are carried out simultaneously in the electrolysis process. Most of the final products obtained by electrolysis are phosphorus oxide, which can not be used in high-end products such as semiconductor materials. In addition, the stability of black phosphorus nanochips is very poor, which is very easy to be oxidized in water or air, and the smaller the number of layers, the faster the oxidation rate. After a large number of tests, the inventor of the invention adds epoxy resin in the electrolysis process and the black phosphorus surface has excellent bonding strength, good dielectric performance, small variable shrinkage, good dimensional stability, high hardness, good flexibility and stability to alkali and most solvents due to the use of epoxy groups in it. Adding a small amount of epoxy resin to the electrolyte will slightly reduce the conductivity of the alkaline aqueous electrolyte, but on the one hand, due to its polymer structure, it can interact with phosphorus on the surface of black phosphorus, reducing the possibility of direct contact between black phosphorus and oxygen or hydroxyl radical in the electrolyte, and the chemical reaction does not affect the exfoliation and intercalation effect between the black phosphorus layer and the layer, which can effectively prevent the oxidation and decomposition of black phosphorus in the electrolysis process; On the other hand, due to the large molecular volume of the epoxy resin itself, the interaction between black phosphorus layers can be weakened to a certain extent in the intercalation process, making the subsequent intercalation easier.

Wherein, the black phosphorus sheet is pressed by the black phosphorus material through the tablet pressing equipment, the thickness of the tablet is 2~5 mm, and the black phosphorus material is one or more of the black phosphorus single crystal and black phosphorus powder.

Wherein the sulfate is selected from one or more of ammonium sulfate, ammonium bisulfate, sodium sulfate, sodium bisulfate, potassium sulfate, and potassium bisulfate.

In addition, the alkaline solution is ammonia, sodium hydroxide solution or potassium hydroxide solution, preferably ammonia. Add ammonia to sulfate solution B, adjust the pH value to 8~10, and stir the mixture at an average speed for 15~20 minutes, and the ultrasonication was performed at 15~30° C. and 30~60 W for 1~10 minutes. Compared with alkaline reagents such as sodium hydroxide and potassium hydroxide, the purity of black phosphorus nanoparticles is higher while the alkaline solution is ammonia; In the process of thermal evaporation, ammonia will be discharged from the black phosphorus layers, which will help the black phosphorus exfoliation and further reduce the number of layers of the exfoliated black phosphorus nanosheets.

Embodiment 1

The preparation method of black phosphorus nanosheet in this embodiment comprises the following steps:

Step S101: electrode selection

The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte

Select ammonium sulfate to prepare 1 mol/L ammonium sulfate solution A and 1 mol/L ammonium sulfate solution B; In ammonium sulfate solution B, 2 ml of 30% ammonia water is added per 100 ml of ammonium sulfate solution B according to the volume ratio of 2 to adjust the pH value of ammonium sulfate solution 13 to 9, stir the mixed solution At an average speed for 15 minutes, and ultrasonic for 5 minutes under the power of 25° C. and 50 W to obtain alkaline aqueous electrolyte C;

Step S103: reaction and exfoliation

Constant temperature environment at 0° C.; Using black phosphorus flake as an anode, platinum electrode as cathode and ammonium sulfate solution A as the electrolyte, it was stable for 2 h at 3V DC voltage; Then, the anode and cathode are transferred to alkaline aqueous electrolyte C, and N-N dimethylformamide solution containing 0.1% epoxy resin is added to alkaline aqueous electrolyte C. The volume ratio of N-N dimethylformamide solution to alkaline aqueous electrolyte C is 1:50, the voltage is stable at 10V, and then powered on for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-N dimethylformamide, and the addition amount of N-N dimethylformamide is 1 ml/mg of the precipitate; Ultrasonication at 25° C. and 100 W power for 30 minutes to obtain D solution, and centrifuge D solution At 3000 rpm for 30 minutes; The upper liquid after centrifugation is filtered and cleaned with deionized water for 10 times to obtain the separated solid;

Step S105: drying

Figure 1:
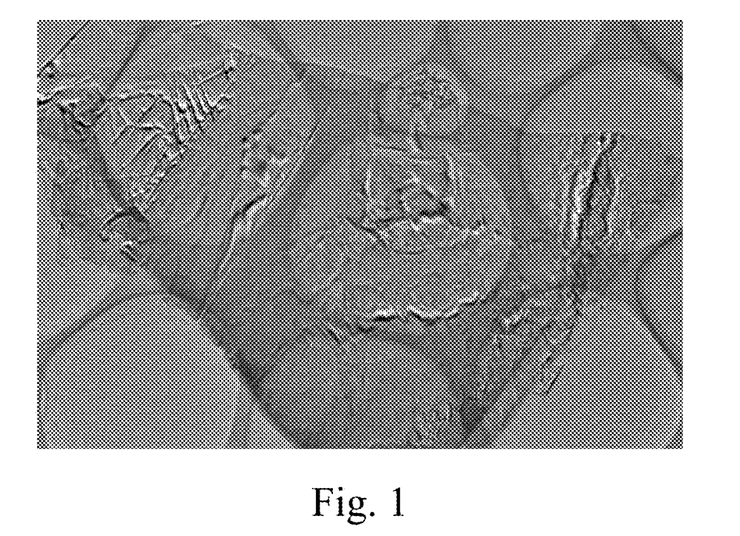
FIG. 1 is a transmission electron microscope view of the black phosphorus nanosheet prepared in embodiment 1.
Figure 2:
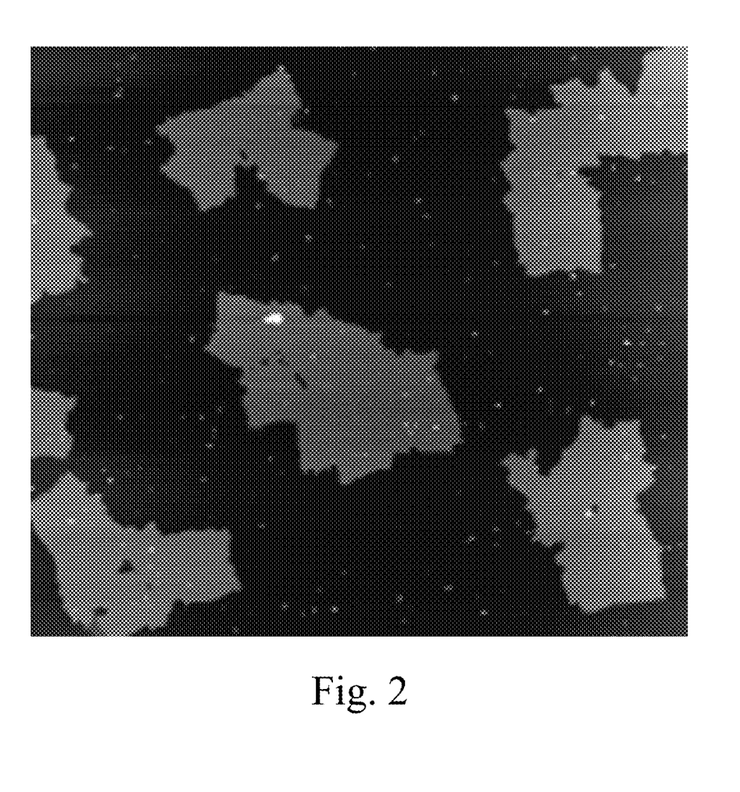
FIG. 2 is an atomic force microscope view of the black phosphorus nanosheet prepared in embodiment 1.
Figure 3:
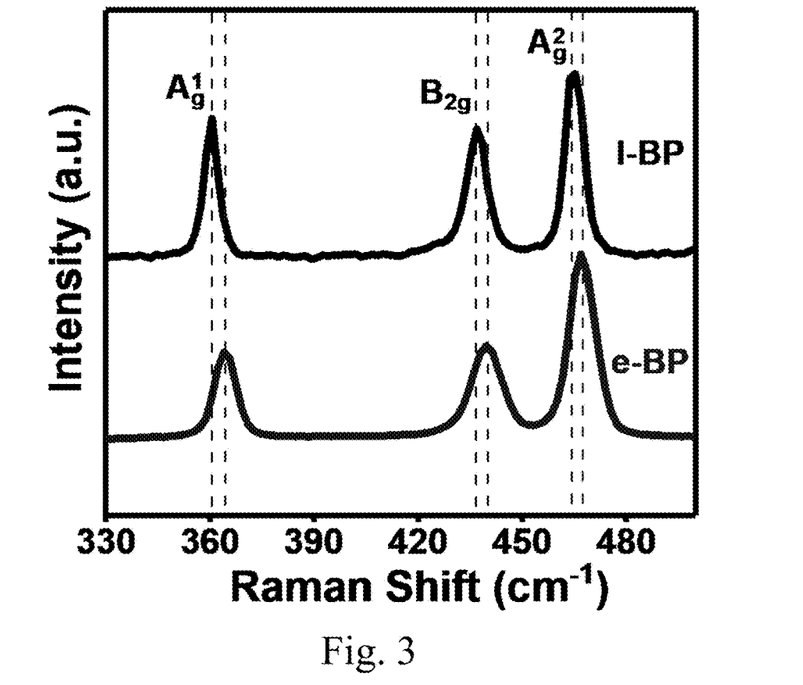
FIG. 3 is a Raman spectrum comparison diagram of the black phosphorus nanosheet prepared in example 1 and the black phosphorus nanosheet prepared by the traditional liquid phase exfoliation process.
Figure 4:
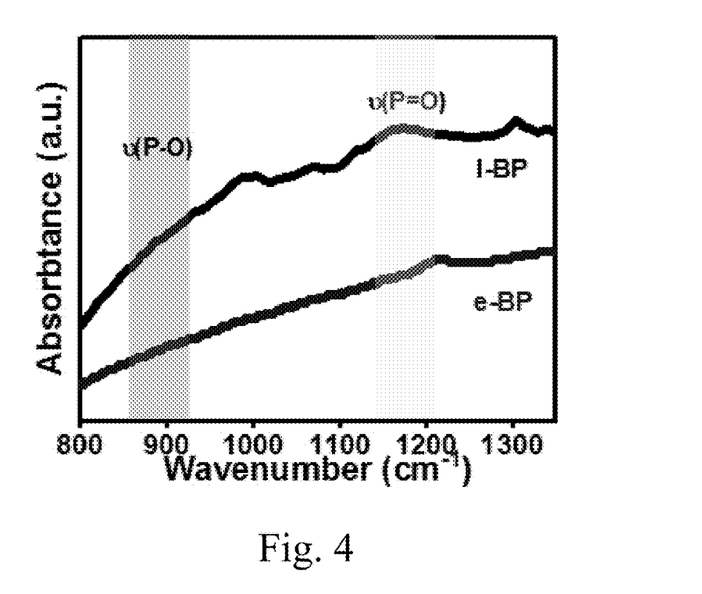
FIG. 4 is an infrared spectrum comparison diagram of the black phosphorus nanosheet prepared in example 1 and the black phosphorus nanosheet prepared by the traditional liquid phase exfoliation process.

The solid separated in step S104 is freeze-dried to obtain black phosphorus nanosheets. The transmission electron microscope and atomic force microscope are shown in FIG. 1 and FIG. 2 respectively, and the Raman and infrared spectra are shown in FIG. 3 and FIG. 4 respectively.

Figure 5:
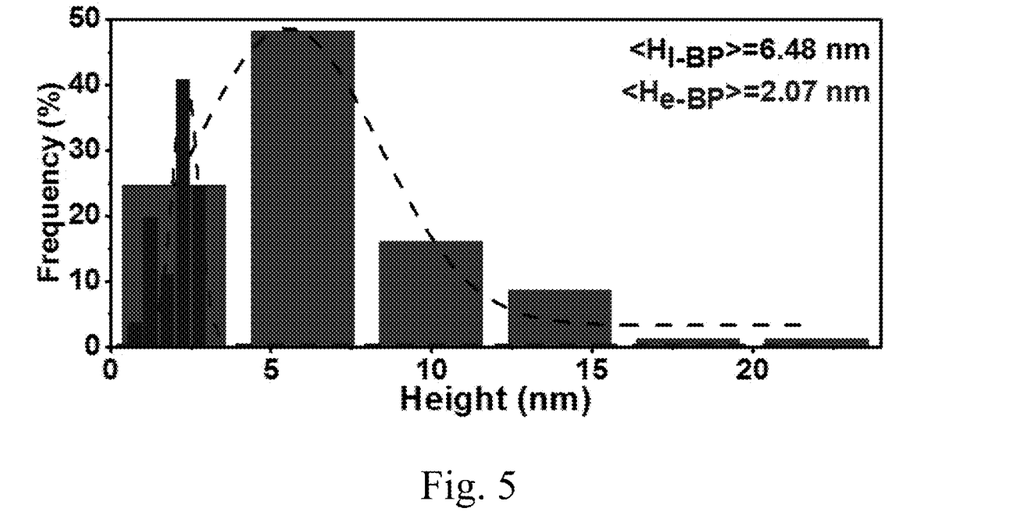
FIG. 5 is a statistical comparison diagram of the thickness between the black phosphorus nanosheet prepared in embodiment 1 and the black phosphorus nanosheet prepared by the traditional liquid phase exfoliation process.
Figure 6:
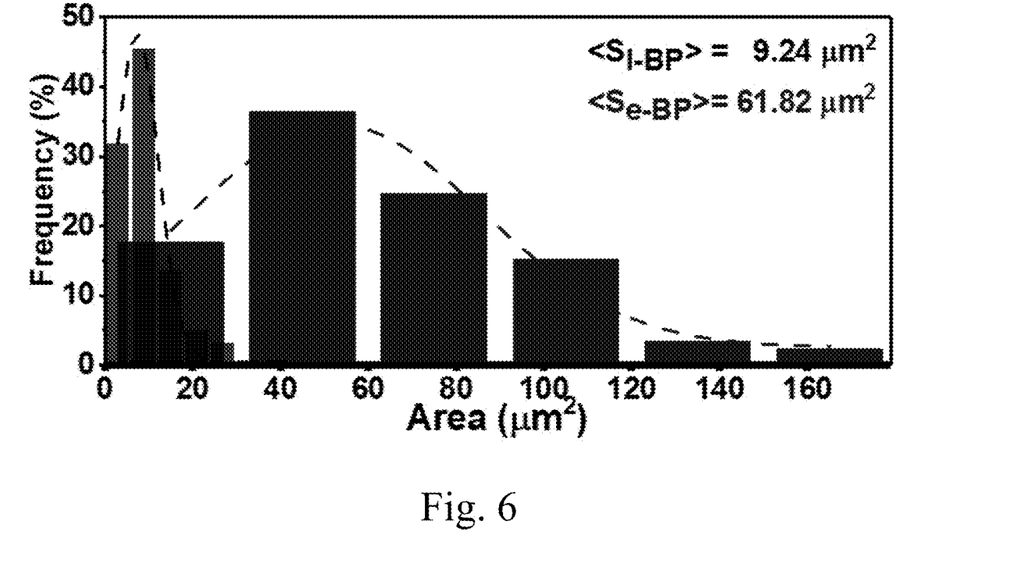
FIG. 6 is a size statistical comparison diagram between the black phosphorus nanosheet prepared in embodiment 1 and the black phosphorus nanosheet prepared by the traditional liquid phase exfoliation process.

The oxygen content of the obtained black phosphorus nanoparticles is about 16%, and the average size is more than 2.5 μm. The number of layers is less than 5, and the statistics of its size and layer thickness are shown in FIG. 5 and FIG. 6.

Comparative Example 1-1

Different from step S102 in embodiment 1, step S102 in this pair of proportions adjusts the pH of the solution by adding sulfuric acid and ammonia respectively. The specific method includes the following steps:

Step S101: electrode selection

The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte (1) Select ammonium sulfate to prepare 1 mol/L ammonium sulfate solution A and 1 mol/L ammonium sulfate solution B; Then, in ammonium sulfate solution B, by controlling the ratio of sulfuric acid and ammonia to make the pH values 1, 4, 7, 10 and 13 respectively, stir the mixed solution at an average speed for 15 minutes, and ultrasonic for 5 minutes at the power of 25 r and 50 W to obtain alkaline aqueous electrolyte C;

Step S103: reaction and exfoliation

Constant temperature environment at 0° C.; Using black phosphorus flake as an anode, platinum electrode as cathode and ammonium sulfate solution A as the electrolyte, it was stable for 2 h at 3V DC voltage; Then, the anode and cathode were transferred to alkaline aqueous electrolyte C, the voltage was stabilized at 10V, and continued to be energized for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-N dimethylformamide, and the addition amount of N-N dimethylformamide is 1 ml/mg of the precipitate; Ultrasonication at 25° C. and 100 W power for 30 minutes to obtain D solution, and centrifuge D solution At 3000 rpm for 30 minutes; The upper liquid after centrifugation is filtered and cleaned with deionized water for 10 times to obtain the separated solid;

Step S105: drying

Figure 7A:
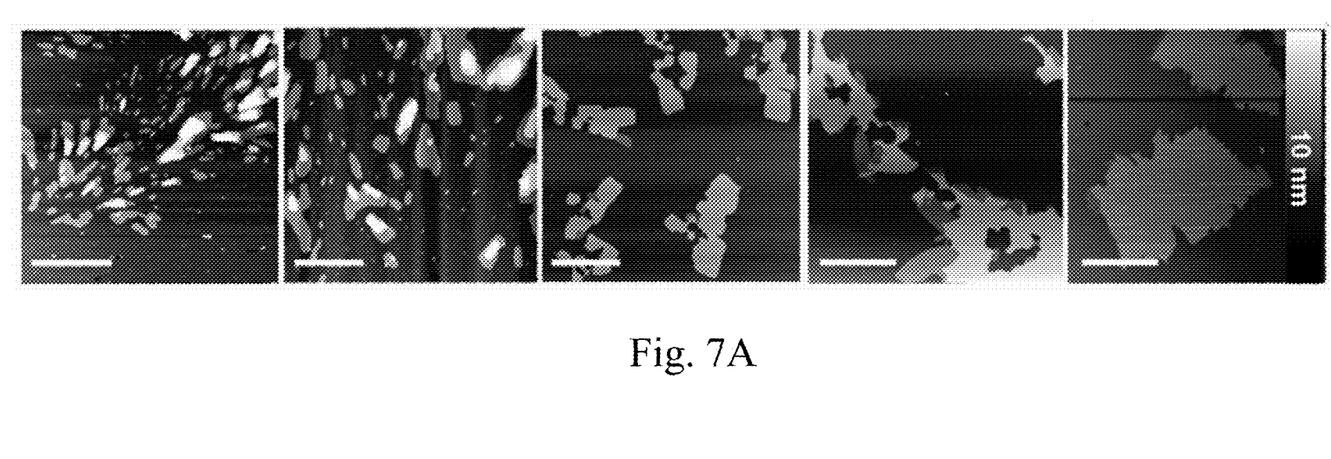
FIG. 7A is a diagram of atomic force microscopy of black phosphorus nanosheets prepared at different pH(pH=1, 4, 10, 13)
Figure 7B:
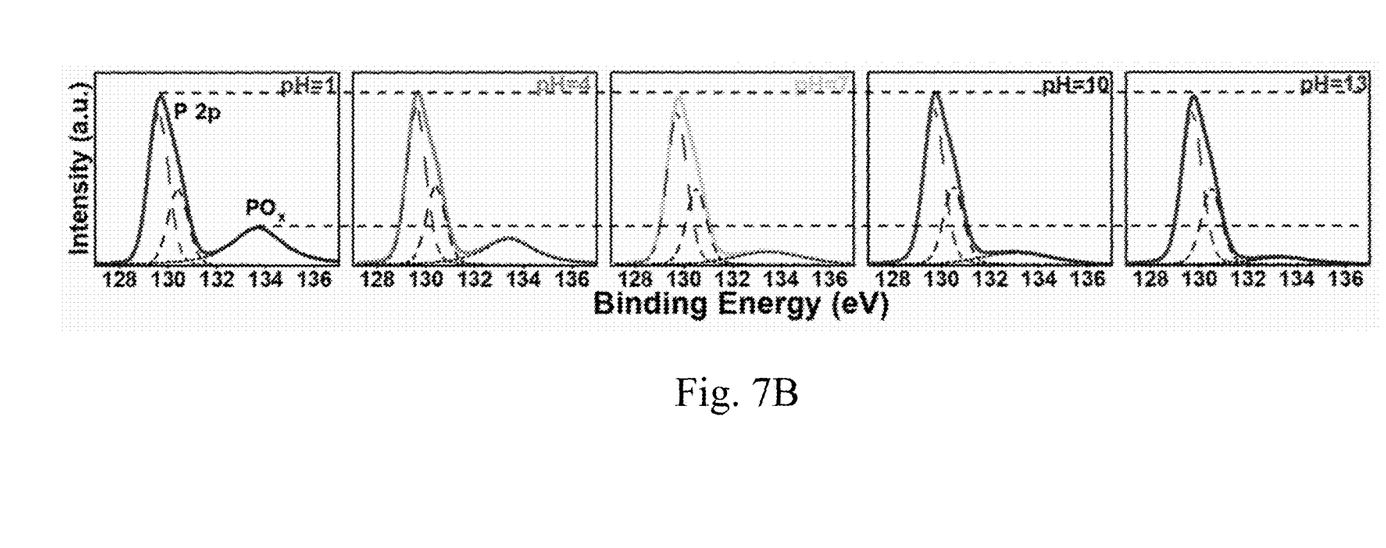
FIG. 7B is X-ray photoelectron spectroscopy P 2p of black phosphorus nanosheets prepared at different pH(pH=1, 4, 10, 13)

The solid separated in step S104 is freeze-dried to obtain black phosphorus nanosheets. The corresponding atomic force microscopy and X-ray photoelectron spectroscopy are shown in FIG. 7A and FIG. 7B. The oxygen content of the high oxidation black phosphorus nanosheets obtained decreases with the increase of pH. The oxidation degree of the black phosphorus prepared under acidic conditions is much higher than that of the black phosphorus nanosheets obtained under alkaline conditions by adding ammonia.

Comparative Example 1-2

Different from step S103 in embodiment 1, step S103 in this pair of proportions does not add N-N dimethylformamide solution dissolved with epoxy resin. The specific method includes the following steps:

The preparation method of the pair of black phosphorus nanosheets comprises the following steps:

Step S101: electrode selection

The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte

Select ammonium sulfate to prepare 1 mol/L ammonium sulfate solution A and 1 mol/L ammonium sulfate solution B; In ammonium sulfate solution B, 2 ml of 30% ammonia water is added per 100 ml of ammonium sulfate solution B according to the volume ratio of 2% to adjust the pH value of ammonium sulfate solution B to 9, stir the mixed solution at an average speed for 15 minutes, and ultrasonic for 5 minutes under the power of 25° C. and 50 W to obtain alkaline aqueous electrolyte C;

Step S103: reaction and exfoliation

Constant temperature environment at 0° C.; Using black phosphorus flake as an anode, platinum electrode as cathode and ammonium sulfate solution A as the electrolyte, it was stable for 2 h at 3V DC voltage; Then, the anode and cathode were transferred to alkaline aqueous electrolyte C, the voltage was stabilized at 10V, and continued to be energized for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-N dimethylformamide, and the addition amount of N-N dimethylformamide is 1 ml/mg of the precipitate; Ultrasonication at 25° C. and 100 W power for 30 minutes to obtain D solution, and centrifuge D solution At 3000 rpm for 30 minutes;

The upper liquid after centrifugation is filtered and cleaned with deionized water for 10 times to obtain the separated solid;

Step S105: drying

The solid separated in step S104 is freeze-dried to obtain black phosphorus nanosheets.

Figure 8:
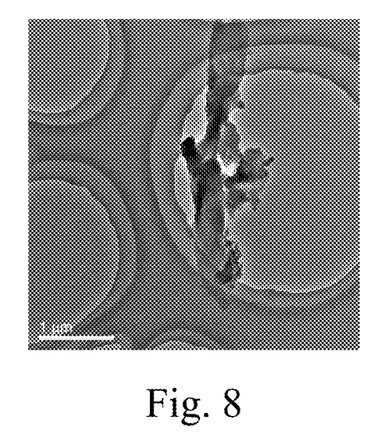
FIG. 8 is a transmission electron microscope view of the black phosphorus nanosheet prepared in proportion 1-2.

The oxygen content of the obtained black phosphorus nanosheet is about 25%, and the average size is more than 1.6 μm. The number of layers is 15, and the transmission electron microscope is shown in FIG. 8.

Embodiment 2

The preparation method of black phosphorus nanosheet in this embodiment comprises the following steps:

Step S101: electrode selection

The black phosphorus powder is pressed into a black phosphorus sheet with a thickness of 4 mm as the anode during electrolysis; The gold electrode is selected as the cathode of electrolysis;

Step S102: prepare alkaline aqueous electrolyte

Select ammonium bisulfate to prepare 0.6 mol/l ammonium bisulfate solution A and 0.6 mol/l ammonium bisulfate solution B; In ammonium bisulfate solution B, 3 ml of 30% ammonia water is added per 100 ml of ammonium bisulfate solution B according to the volume ratio of 3% to adjust the pH value of ammonium bisulfate solution B to 10, stir the mixture at an average speed for 15 minutes, and ultrasonic for 5 minutes under the power of 25° C. and 40 W to obtain alkaline aqueous electrolyte C;

Step S103: reaction and exfoliation

At 2° C. constant temperature environment; With black phosphorus sheet as an anode, gold electrode as cathode, and ammonium hydrogen sulfate solution A as the electrolyte, it is stable for 1.5 h under 3V DC voltage; Then, the anode and cathode are transferred to alkaline aqueous electrolyte C, and N-N dimethylformamide solution containing 0.5% epoxy resin is added to alkaline aqueous electrolyte C. The volume ratio of N-N dimethylformamide solution to alkaline aqueous electrolyte C is 1:100, the voltage is stable at 10V, and then powered on for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-N dimethylformamide, and the addition amount of N-N dimethylformamide is 1 ml/mg of the precipitate; Ultrasonication at 25 and 100 W power for 30 minutes to obtain D solution, and centrifuge D solution at 3000 rpm for 30 minutes; The upper liquid after centrifugation is filtered and cleaned with deionized water for 8 times to obtain the separated solid;

Step S105: drying

The solid separated in step S104 is vacuum dried to obtain black phosphorus nanosheets.

The oxygen content of the obtained black phosphorus nanosheet is about 12%, and the average size is more than 3 μm. The number of floors is less than 10.

Embodiment 3

The preparation method of black phosphorus nanosheet in this embodiment comprises the following steps:

Step S101: electrode selection

The black phosphorus powder is pressed into a black phosphorus sheet with a thickness of 2 mm as the anode during electrolysis; Platinum electrode is selected as the cathode of electrolysis;

Step S102: prepare alkaline aqueous electrolyte

Select sodium sulfate to prepare 0.6 mol/l sodium sulfate solution A and 0.6 mol/l sodium sulfate solution B; In sodium sulfate solution B, according to the volume ratio of 4%, that is, add 4 ml of 30% mass fraction of ammonia per 100 ml of sodium sulfate solution B to adjust the pH value of sodium sulfate solution B to 11, stir the mixture at an average speed for 20 minutes, and ultrasonic for 7 minutes under the power of 25 and 50 W to obtain alkaline aqueous electrolyte C;

Step S103: reaction and exfoliation

At 3° C. constant temperature environment, using black phosphorus flake as an anode, platinum electrode as cathode, and sodium sulfate solution A as the electrolyte, it was stable for 1H at 3V DC voltage; Then, the anode and cathode are transferred to the alkaline aqueous electrolyte C. at the same time, N-N dimethylformamide solution containing 1% epoxy resin is added to the alkaline aqueous electrolyte C. the volume ratio of N-N dimethylformamide solution to alkaline aqueous electrolyte C is 1:150, the voltage is stable at 6V, continue to be energized for 0.5 h, and black phosphorus nanosheet precipitation is obtained at the bottom of alkaline aqueous electrolyte C;

Step S104: cleaning and extraction

Dissolve the precipitate obtained by the reaction in step S103 in the organic solvent N-methylpyrrolidone, and the addition amount of N-methylpyrrolidone is 1 ml/mg of the precipitate; Ultrasonication at 25° C. and 100 W power for 30 minutes to obtain D solution, and centrifuge D solution at 3000 rpm for 30 minutes; The upper liquid after centrifugation is filtered and cleaned with deionized water for 10 times to obtain the separated solid;

Step S105: drying

The solid separated in step S104 is freeze-dried to obtain black phosphorus nanosheets.

The oxygen content of the obtained black phosphorus nanoparticles is about 16%, and the average size is more than 5.4 μm, and the number of layers is less than 7.

Embodiment 4

The preparation method of black phosphorus nanosheet in this embodiment comprises the following steps:

Step S101: electrode selection

The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte

Select sodium bisulfate to prepare 1 mol/L sodium bisulfate solution A and 1 mol/L sodium bisulfate solution B; In sodium bisulfate solution B, 3 ml of 30% mass fraction ammonia is added per 100 ml of sodium bisulfate solution B according to the volume ratio of 3% to adjust the pH value of sodium bisulfate solution B to 10, stir the mixture at an average speed for 20 minutes, and ultrasonic for 10 minutes under the power of 25° C. and 60 W to obtain alkaline aqueous electrolyte C;

Step S103: reaction and exfoliation

Constant temperature environment at 0° C.; Using black phosphorus sheet as an anode, platinum electrode as cathode and sodium bisulfate solution A as the electrolyte, it was stable for 1.5 h at 3V DC voltage; Then, the anode and cathode are transferred to alkaline aqueous electrolyte C, and N-N dimethylformamide solution containing 1.5% epoxy resin is added to alkaline aqueous electrolyte C, the volume ratio of N-N dimethylformamide solution to alkaline aqueous electrolyte C is 1:120, the voltage is stable at 12V, and then powered on for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent isopropanol, and the amount of isopropanol is 1 ml/mg of the precipitate; Ultrasonication at 25° C. and 100 W power for 40 minutes to obtain D solution, and centrifuge D solution At 2000 rpm for 40 minutes; The upper liquid after centrifugation is filtered and cleaned with deionized water for 7 times to obtain the separated solid;

Step S105: drying

The solid separated in step S104 is vacuum dried to obtain black phosphorus nanosheets.

The oxygen content of the obtained black phosphorus nanosheet is about 13%, and the average size is more than 3 μm, and the number of floors is less than 9.

Embodiment 5

The preparation method of black phosphorus nanosheet in this embodiment comprises the following steps:

Step S101: electrode selection

The black phosphorus powder is pressed into a black phosphorus sheet with a thickness of 5 mm as the anode during electrolysis; Platinum electrode is selected as the cathode of electrolysis;

Step S102: prepare alkaline aqueous electrolyte

Select potassium sulfate to prepare 2 mol/L potassium sulfate solution A and 2 mol/L potassium sulfate solution B; In potassium sulfate solution B, 2 ml of 30% ammonia water is added per 100 ml of potassium sulfate solution B according to the volume ratio of 2%, to adjust the pH value of potassium sulfate solution B to 10, stir the mixed solution At an average speed for 15 minutes, and ultrasonic for 5 minutes under the power of 25° C. and 50 W to obtain alkaline aqueous electrolyte C;

Step S103: reaction and exfoliation

Constant temperature environment at 0° C. Using black phosphorus flake as an anode, platinum electrode as cathode and potassium sulfate solution A as the electrolyte, it was stable for 2 h at 3V DC voltage; Then, the anode and cathode are transferred to alkaline aqueous electrolyte C, and N-N dimethylformamide solution containing 0.5% epoxy resin is added to alkaline aqueous electrolyte C. The volume ratio of N-N dimethylformamide solution to alkaline aqueous electrolyte C is 1:120, the voltage is stable at 10V, and then powered on for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-methylpyrrolidone, and the addition amount of N-methylpyrrolidone is 2 ml/mg of the precipitate; Ultrasonication at 25° C. and 100 W power for 20 minutes to obtain D solution, and centrifuge D solution at 4000 rpm for 20 minutes; The upper liquid after centrifugation is filtered and cleaned with deionized water for 10 times to obtain the separated solid;

Step S105: drying

The solid separated in step S104 is freeze-dried to obtain black phosphorus nanosheets.

The oxygen content of the obtained black phosphorus nanosheet is about 15%, and the average size is more than 5 μm, and the number of layers is less than 6.

Embodiment 6

The preparation method of black phosphorus nanosheet in this embodiment comprises the following steps:

Step S101: electrode selection

The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte

Select ammonium sulfate to prepare 1 mol/L ammonium sulfate solution A and 1 mol/L ammonium sulfate solution B; Add 2 ml of 10% sodium hydroxide solution to 100 ml ammonium sulfate solution B according to the volume ratio of 2% to adjust the pH value of ammonium sulfate solution B to 9, stir the mixed solution at an average speed for 15 minutes, and ultrasonic for 5 minutes under the power of 25° C. and 50 W to obtain alkaline aqueous electrolyte C;

Step S103: reaction and exfoliation

Constant temperature environment at 0° C.; Using black phosphorus flake as an anode, platinum electrode as cathode and ammonium sulfate solution A as the electrolyte, it was stable for 2 h at 3V DC voltage; Then, the anode and cathode are transferred to alkaline aqueous electrolyte C, and N-N dimethylformamide solution containing 0.1% epoxy resin is added to alkaline aqueous electrolyte C. The volume ratio of N-N dimethylformamide solution to alkaline aqueous electrolyte C is 1:50, the voltage is stable at 10V, and then powered on for 1 h to obtain black phosphorus nanosheet precipitation at the bottom of alkaline aqueous electrolyte C;

Step S104: cleaning and extraction

Dissolve the precipitate obtained by the reaction in step S103 in the organic solvent N-N dimethylformamide, and the addition amount of N-N dimethylformamide is 1 ml/mg of the precipitate; Ultrasonication at 25° C. and 100 W power for 30 minutes to obtain D solution, and centrifuge D solution at 3000 rpm for 30 minutes; The upper liquid after centrifugation is filtered and cleaned with deionized water for 10 times to obtain the separated solid;

Step S105: drying

The solid separated in step S104 is freeze-dried to obtain black phosphorus nanosheets.

Although the oxygen content of the obtained black phosphorus nanoparticles is about 18%, and the average size is more than 2.5 μm, and the number of layers is less than 10, but the residual sodium ion is greater than 150 ppm.

Embodiment 7

The preparation method of black phosphorus nanosheet in this embodiment comprises the following steps:

Step S101: electrode selection
The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte
Select ammonium sulfate to prepare 1 mol/L ammonium sulfate solution A and 1 mol/L ammonium sulfate solution B; Add 2 ml of 10% potassium hydroxide solution to 100 ml ammonium sulfate solution B according to 2% volume ratio to adjust the pH value of ammonium sulfate solution B to 9, stir the mixture at an average speed for 15 minutes, and ultrasonic for 5 minutes at 25° C. and 50 W power to obtain alkaline aqueous electrolyte C;

Step S103: reaction and exfoliation
Constant temperature environment at 0° C.; Using black phosphorus flake as an anode, platinum electrode as cathode and ammonium sulfate solution A as the electrolyte, it was stable for 2 h at 3V DC voltage; Then, the anode and cathode are transferred to alkaline aqueous electrolyte C, and N-N dimethylformamide solution containing 0.1% epoxy resin is added to alkaline aqueous electrolyte C. The volume ratio of N-N dimethylformamide solution to alkaline aqueous electrolyte C is 1:50, the voltage is stable at 10V, and then powered on for 1 h to obtain black phosphorus nanosheet precipitation at the bottom of alkaline aqueous electrolyte C;

Step S104: cleaning and extraction
Dissolve the precipitate obtained by the reaction in step S103 in the organic solvent N-N dimethylformamide, and the addition amount of N-N dimethylformamide is 1 ml/mg of the precipitate; Ultrasonication at 25° C. and 100 W power for 30 minutes to obtain D solution, and centrifuge D solution at 3000 rpm for 30 minutes; The upper liquid after centrifugation is filtered and cleaned with deionized water for 10 times to obtain the separated solid;

Step S105: drying
The solid separated in step S104 is freeze-dried to obtain black phosphorus nanosheets.

Although the oxygen content of the obtained black phosphorus nanoparticles is about 17%, and the average size exceeds 2.1 μm, the number of layers is less than 11, but the residual potassium ion is greater than 200 ppm.

Comparative Example 3

Different from step S104 in embodiment 1, step S104 in this comparative example adjusts the size of the obtained black phosphorus nanosheet by changing the time of different ultrasonication conditions: the preparation method of this pair of proportional black phosphorus nanosheets includes the following steps:

Step S101: electrode selection
The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte
Select ammonium sulfate to prepare 1 mol/L ammonium sulfate solution A and 1 mol/L ammonium sulfate solution B; In ammonium sulfate solution B, 2 ml of 30% ammonia water is added per 100 ml of ammonium sulfate solution B according to the volume ratio of 2% to adjust the pH value of ammonium sulfate solution B to 9, stir the mixed solution At an average speed for 15 minutes, and ultrasonic for 5 minutes under the power of 25 V and 50 W to obtain alkaline aqueous electrolyte C;

Step S103: reaction and exfoliation
Constant temperature environment at 0° C.; Using black phosphorus flake as an anode, platinum electrode as cathode and ammonium sulfate solution A as the electrolyte, it was stable for 2 h at 3V DC voltage; Then, the anode and cathode are transferred to alkaline aqueous electrolyte C, and N-N dimethylformamide solution containing 0.1% epoxy resin is added to alkaline aqueous electrolyte C. The volume ratio of N-N dimethylformamide solution to alkaline aqueous electrolyte C is 1:100, the voltage is stable at 10V, and then powered on for 1 h to obtain black phosphorus nanosheet precipitation at the bottom of alkaline aqueous electrolyte C;

Step S104: cleaning and extraction
Dissolve the precipitate obtained by the reaction in step S103 in the organic solvent N-N dimethylformamide, and the addition amount of N-N dimethylformamide is 1 ml/mg of the precipitate; At 25° C. and 100 W power, ultrasonic for different times, 10, 30, 60, and 120 minutes respectively, to obtain D solution, and centrifuge D solution at 3000 rpm for 30 minutes; The upper liquid after centrifugation is filtered and cleaned with deionized water for 10 times to obtain the separated solid;

Step S105: drying
Freeze drying the solid separated in step S104 to obtain black phosphorus nanosheets; The size distribution with ultrasonic time is shown in FIG. 8.

Comparative Example 4

Different from step S104 in embodiment 1, step S104 in this comparative example adjusts the dispersion of black phosphorus nanosheets by changing different ultrasonic solvents. The preparation method of this pair of proportional black phosphorus nanosheets includes the following steps:

Step S101: electrode selection
The black phosphorus single crystal is pressed into a black phosphorus sheet with a thickness of 3 mm as the anode during electrolysis; Platinum electrode is selected as the cathode of electrolysis;

Step S102: prepare alkaline aqueous electrolyte
Select ammonium sulfate to prepare 1 mol/L ammonium sulfate solution A and 1 mol/L ammonium sulfate solution B; In ammonium sulfate solution B, 2 ml of 30% ammonia water is added per 100 ml of ammonium sulfate solution B according to the volume ratio of 2% to adjust the pH value of ammonium sulfate solution B to 9, stir the mixed solution at an average speed for 15 minutes, and ultrasonic for 5 minutes under the power of 25° C. and 50 W to obtain alkaline aqueous electrolyte C;

Step S103: reaction and exfoliation
Constant temperature environment at 0° C.; Using black phosphorus flake as the anode, platinum electrode as cathode, and ammonium sulfate solution A as the electrolyte, it was stable for 2 h at 3V DC voltage; Then, the anode and cathode are transferred to alkaline aqueous electrolyte C, and N-N dimethylformamide solution containing 0.1% epoxy resin is added to alkaline aqueous electrolyte C. The volume ratio of N-N dimethylformamide solution to alkaline aqueous electrolyte C is 1:100, the voltage is stable at 10V, and then powered on for 1 h to obtain black phosphorus nanosheet precipitation at the bottom of alkaline aqueous electrolyte C;

Step S104: cleaning and extraction

The precipitate obtained by the reaction in step S103 is dissolved in three organic solvents: N-N dimethylformamide, N-methyl pyrrolidone, and isopropanol. The addition amount of organic solvents is 1 ml/mg of the precipitate; At 25° C. and 100 W power, ultrasonic for different times, 10, 30, 60, and 120 minutes respectively, to obtain D solution, and centrifuge D solution at 3000 rpm for 30 minutes; The upper liquid after centrifugation is filtered and cleaned with deionized water for 10 times to obtain the separated solid;

Step S105: drying

Figure 9:
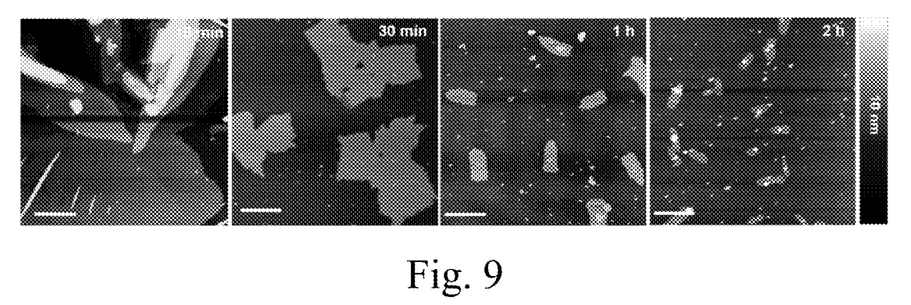
FIG. 9 is an AFM diagram of black phosphorus nanosheets prepared at different ultrasonic times under the control of other conditions unchanged.
Figure 10A:
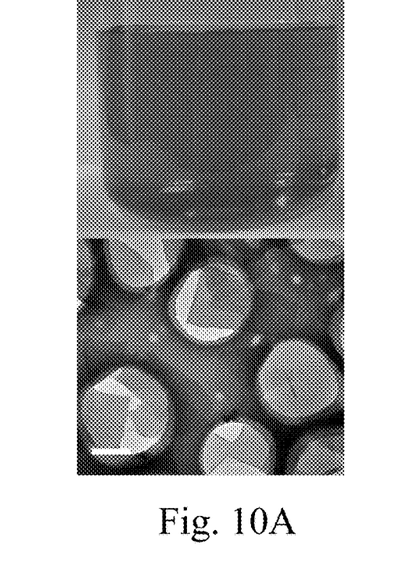
FIG. 10A is a transmission electron microscope view of black phosphorus nanosheets prepared using isopropanol as an ultrasonic solvent.
Figure 10B:
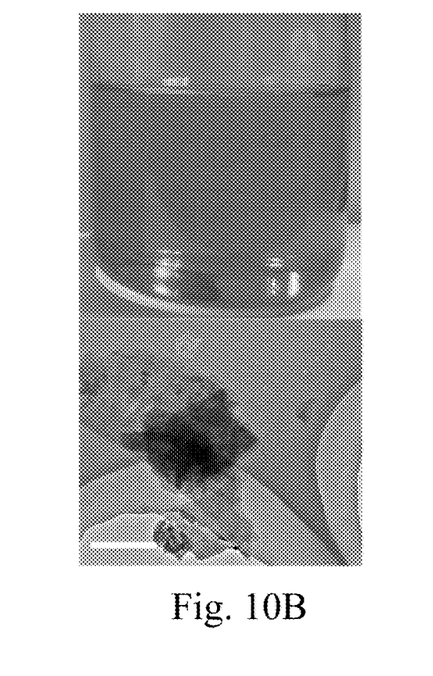
FIG. 10B is a transmission electron microscope view of black phosphorus nanosheets prepared using N-methyl pyrrolidone as an ultrasonic solvent.
Figure 10C:
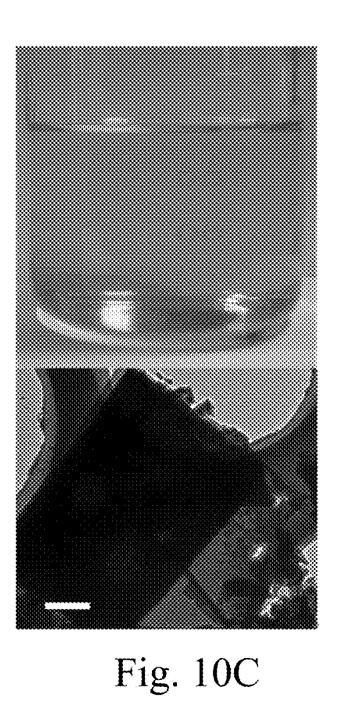
FIG. 10C is a transmission electron microscope view of black phosphorus nanosheets prepared using N-N dimethylformamide as an ultrasonic solvent.

Freeze drying the solid separated in step S104 to obtain black phosphorus nanosheets; After Ultrasonication in different organic solutions, the dispersion is shown in FIG. 9.

By adding ammonia into the electrolyte, the structure of the prepared black phosphorus nanosheet tends to be more stable, not easy to be damaged, and the degree of oxidation is reduced. Compared with the previous method, the intrinsic black phosphorus nanosheet with a higher intrinsic degree can be obtained; At the same time, due to the addition of ammonia, the solution can ionize more hydroxyl ions and gather at the anode, which is more conducive to improve the intercalation exfoliation effect of the black phosphorus material of the anode and make the black phosphorus exfoliation more complete. The exfoliated black phosphorus nanosheet has less layers and larger size, as shown in FIG. 1 and FIG. 2; By comparing the Raman spectrum and infrared spectrum of the black phosphorus nanosheet prepared by the traditional liquid phase exfoliation process with the black phosphorus nanosheet prepared by the method (FIG. 3 and FIG. 4), the eigenvalue of the product prepared by the invention is close to the black phosphorus nanosheet prepared by the traditional liquid phase exfoliation; Through the statistical analysis of the size and thickness of the black phosphorus nanosheet prepared by the traditional liquid phase exfoliation process and the black phosphorus nanosheet prepared by the method (FIG. 5 and FIG. 6), the black phosphorus nanosheet obtained by the invention is closer to the black phosphorus nanosheet in thickness and generally larger in size than the black phosphorus nanosheet obtained by liquid phase exfoliation; It can be seen from the comparison of X-ray photoelectron spectroscopy and atomic force microscope in example 1 and Comparative Example 1 that after ammonia is added to adjust the pH value of electrolyte to alkaline, the oxygen content of black phosphorus nanosheet decreases significantly and the size also increases significantly (FIG. 7); By controlling the ultrasonic time and ultrasonic solvent (FIG. 8 and FIG. 9), the number and size of the product black phosphorus nanosheet are further controlled.

Finally, it should be noted that the above embodiments are only used to illustrate the technical scheme of the invention rather than limit the technical scheme. It should be noted that for ordinary technicians in the technical field, several improvements or equivalent substitutions can be made without departing from the principle of the invention without departing from the purpose and scope of the technical scheme, Both shall be covered by the claims of the invention.

What is claimed is:

1. A method of preparing a black phosphorous nanosheet, the method comprising:

preparing an alkaline aqueous electrolyte by:
1) preparing 0.1~2 mol/L of a sulfate solution A and 0.1~2 mol/L of a sulfate solution B, adding an alkaline solution to the sulfate solution B to adjust the pH value of sulfate solution B to 8~14, and mixing evenly to obtain an alkaline aqueous electrolyte C, and
2) preparing an N-N dimethylformamide solution in which an epoxy resin is dissolved;

performing an electrochemical reaction in a constant temperature environment of 0~10° C., with a black phosphorus sheet as an anode, an inert electrode as a cathode, and the sulfate solution A as an electrolyte, and a surface current density of 200~500 mA/dm$^2$ under a DC voltage of 2.5~3.5V for 1~3 h;

transferring the anode and the cathode to the alkaline aqueous electrolyte C, and adding the N-N dimethylformamide solution with dissolved epoxy resin to the alkaline aqueous electrolyte C; and applying a voltage of 5~10V between the anode and the cathode, wherein the distance between electrodes remains unchanged, the area current density is controlled at 600~900 mA/dm$^2$, and precipitating black phosphorus for the black phosphorous nanosheet at the bottom of the alkaline aqueous electrolyte C for 0.5~1.5 h.

2. The method according to claim 1, wherein the mass ratio of epoxy resin to N-N dimethylformamide is 0.1~2%.

3. The method according to claim 2, wherein the mass ratio of the epoxy resin to N-N dimethylformamide is 0.5~1%.

4. The method according to claim 1, wherein the volume ratio of N-N dimethylformamide solution dissolved with epoxy resin to alkaline aqueous electrolyte C is 1:50~1:200.

5. The method according to claim 1, wherein the volume ratio of N-N dimethylformamide solution dissolved with epoxy resin to alkaline aqueous electrolyte C is 1:100~1:120.

6. The method according to claim 1, wherein the black phosphorus sheet is pressed by a black phosphorus material through tablet pressing equipment, and the black phosphorus material is one or more of black phosphorus single crystal and black phosphorus powder.

7. The method according to claim 1, wherein the sulfate is selected from one or more of ammonium sulfate, ammonium bisulfate, sodium sulfate, sodium bisulfate, potassium sulfate, and potassium bisulfate.

8. The method according to claim 1, wherein the alkaline solution is an ammonia solution, a sodium hydroxide solution, or a potassium hydroxide solution.

9. The method according to claim 8, wherein the alkaline solution is ammonia, ammonia is added to sulfate solution B to the pH value to 8~10, the mixed solution is stirred for 15~20 minutes, and ultrasonication is performed at 15~30° C. and 30~60 W for 1~10 minutes.

10. The method according to claim 1, wherein the inert electrode is a platinum electrode, a gold electrode, or a carbon rod.

11. The method according to claim 1, further comprising:
dissolving the precipitate in an organic solvent, and ultrasonicating for 20 to 40 minutes at a power of 30 to 100 W at room temperature to obtain solution D;
centrifuging the D solution at a rate of 2000~4000 rpm for 20~40 minutes; and
filtering an upper liquid after centrifugation and cleaning with deionized water for 5~10 times to obtain a separated solid.

12. The method according to claim 11, wherein the organic solvent is one or more of N-N dimethylformamide, N-methyl pyrrolidone, dimethyl sulfoxide, and isopropanol, and the amount of the organic solvent is 1-2 ml/mg of the precipitate.

13. The method according to claim 11, further comprising cleaning and recovering the lower precipitation after centrifugation for reuse.

14. The method according to claim 11, further comprising:

drying the separated solid to obtain the black phosphorus nanosheet.

15. The method according to claim 14, wherein the drying is vacuum drying or freeze-drying.

\* \* \* \* \*